(12) United States Patent
Nicolas-Morgantini et al.

(10) Patent No.: US 7,867,478 B2
(45) Date of Patent: *Jan. 11, 2011

(54) REDUCING COMPOSITION FOR PERMANENTLY RESHAPING OR STRAIGHTENING THE HAIR, CONTAINING A CERTAIN AMOUNT OF MESOMORPHIC PHASE, PROCESS FOR PREPARING IT AND PROCESS FOR PERMANENTLY RESHAPING OR STRAIGHTENING THE HAIR

(75) Inventors: Luc Nicolas-Morgantini, Rully (FR); Jean-Marc Petit, Clichy (FR)

(73) Assignee: L'Oreal S.A., Paris (FR)

( * ) Notice: Subject to any disclaimer, the term of this patent is extended or adjusted under 35 U.S.C. 154(b) by 1325 days.

This patent is subject to a terminal disclaimer.

(21) Appl. No.: 10/745,366

(22) Filed: Dec. 24, 2003

(65) Prior Publication Data
US 2005/0042190 A1 Feb. 24, 2005

Related U.S. Application Data

(60) Provisional application No. 60/469,405, filed on May 12, 2003.

(30) Foreign Application Priority Data

Dec. 24, 2002 (FR) ................................. 02 16597

(51) Int. Cl.
*A61Q 5/04* (2006.01)
(52) U.S. Cl. .................................. 424/70.2; 424/70.31
(58) Field of Classification Search ........................ None
See application file for complete search history.

(56) References Cited

U.S. PATENT DOCUMENTS

| | | | |
|---|---|---|---|
| 3,768,490 A | 10/1973 | Kalopissis et al. | |
| 3,975,515 A | 8/1976 | Wajaroff et al. | |
| 4,366,827 A | 1/1983 | Madrange et al. | |
| 4,394,520 A | 7/1983 | Kalopissis | |
| 4,533,714 A | 8/1985 | Sebag et al. | |
| 4,548,811 A | 10/1985 | Kubo et al. | |
| 4,560,554 A | 12/1985 | Kubo et al. | |
| 4,587,321 A | 5/1986 | Sebag et al. | |
| 4,749,732 A | 6/1988 | Kohl et al. | |
| 4,781,724 A * | 11/1988 | Wajaroff et al. | 8/426 |
| 4,880,618 A | 11/1989 | Grollier et al. | |
| 4,956,175 A | 9/1990 | Maignan et al. | |
| 4,996,059 A | 2/1991 | Grollier et al. | |
| 5,015,767 A | 5/1991 | Maignan et al. | |
| 5,021,200 A * | 6/1991 | Vanlerberghe et al. | 264/4.3 |
| 5,085,860 A | 2/1992 | Junino et al. | |
| 5,106,612 A | 4/1992 | Maignan et al. | |
| 5,334,377 A | 8/1994 | Junino et al. | |
| 5,449,805 A | 9/1995 | Junino et al. | |
| 5,466,878 A | 11/1995 | Junino et al. | |
| 5,583,257 A | 12/1996 | Junino et al. | |
| 5,958,392 A | 9/1999 | Grollier et al. | |
| 6,173,717 B1 | 1/2001 | Schonert et al. | |
| 6,572,663 B1 | 6/2003 | Pitfield et al. | |
| 6,871,652 B1 * | 3/2005 | Mueller et al. | 132/202 |
| 6,991,781 B2 * | 1/2006 | Glenn et al. | 424/70.1 |
| 2001/0023514 A1 * | 9/2001 | Cottard et al. | 8/406 |
| 2004/0034946 A1 | 2/2004 | Legrand et al. | |

FOREIGN PATENT DOCUMENTS

| | | |
|---|---|---|
| EP | 0 295 780 | 12/1988 |
| EP | 0 312 343 | 4/1989 |
| FR | 1 313 557 | 11/1962 |
| GB | 1199776 | 7/1970 |
| GB | 2 026 052 A | 1/1980 |
| GB | 2197352 | 5/1988 |
| WO | WO 99/30676 | 6/1999 |

OTHER PUBLICATIONS

English language Abstract of EP 0 368 763, May 16, 1990.
English language Abstract of FR 2 679 448, Jan. 29, 1993.
English language Derwent Abstract of LU 83703, Jun. 8. 1983.
Charvolin, J. et al., La Recherche, vol. 23, Mar. 1992, pp. 306-315.
Engstrom, S., Lipid Technology, vol. 2, No. 2, Apr. 1990, pp. 42-45.
Griffin, W., "Calculation of HLB Values of Non-Ionic Surfactants", J. Soc. Cosm. Chem. 1954 (vol. 5), pp. 249-256.

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

The present disclosure relates to reducing compositions comprising, in an aqueous medium, at least one compound for reducing keratin, ammonia, and at least one mesomorphic phase present in an amount of at least 10% by weight, relative to the weight of the composition. The mesomorphic phase generally comprises nonionic surfactants with an HLB value of less than or equal to 10. The present disclosure also relates to the process for preparing the compositions, and to a process for permanently reshaping or straightening the hair using the reducing compositions, as well as multi-compartment kits for permanently reshaping or straightening the hair, wherein at least one compartment contains the reducing composition.

20 Claims, No Drawings

OTHER PUBLICATIONS

Small, D.M , "The Physical Chemistry of Lipids from Alkanes to Phospholipids", Handbook of Lipid Research 4, 1986, Plenum Press, pp. 51-56.

WO 97/04738, Abstract (Feb. 13, 1997).

English Language Derwent Abstract of DE 40 05 008.

International Search Report of FR 02 16599 (priority application of co-pending U.S. Appl. No. 10/743,004) dated Jun. 19, 2003.

Co-pending U.S. Appl. No. 10/743,004.

Office Action of U.S. Appl. No. 10/743,004 dated Dec. 6, 2005.

Final Office Action of U.S. Appl. No. 10/743,004 dated Jul. 10, 2006.

Advisory Action of U.S. Appl. No. 10/743,004 dated Jan. 30, 2007.

Office Action of U.S. Appl. No. 10/743,004 dated Sep. 24, 2007.

Final Office Action of U.S. Appl. No. 10/743,004 dated May 16, 2008.

WO 02/41983 (May 2002) Abstract.

Notice of Allowance dated Jun. 26, 2009, in U.S. Appl. No. 10/743,004 (issued as U.S. Patent No. 7,608,116, on Oct. 27, 2009).

* cited by examiner

REDUCING COMPOSITION FOR PERMANENTLY RESHAPING OR STRAIGHTENING THE HAIR, CONTAINING A CERTAIN AMOUNT OF MESOMORPHIC PHASE, PROCESS FOR PREPARING IT AND PROCESS FOR PERMANENTLY RESHAPING OR STRAIGHTENING THE HAIR

This application claims the benefit of priority to U.S. Provisional Application No. 60/469,405, filed May 12, 2003, the contents of which are incorporated herein by reference. This application also claims benefit of priority under 35 U.S.C. §119 to French Patent Application No. 02 16597, filed Dec. 24, 2002, the contents of which are also incorporated herein by reference.

The present disclosure relates to a reducing composition for permanently reshaping or straightening the hair, to a process for preparing the composition, to a permanent-reshaping or straightening process using the composition, as well as to a multi-compartment kit containing the composition.

One of the techniques commonly used in cosmetics to give the hair a long-lasting shape comprises reshaping the hair using a reducing compound and then an oxidizing compound.

The technique most commonly used for permanently reshaping the hair initially comprises opening the disulphide (—S—S—) bonds of keratin (cysteine) using a composition containing a reducing compound. After the head of hair thus treated has been rinsed, reconstituting of the disulphide bonds occurs by applying an oxidizing composition, also known as a "fixative", to the hair which has been placed under tension beforehand with rollers or other means, so as to give the hair the desired shape.

This technique thus makes it possible either to make the hair wavy or to straighten it or uncurl it, or alternatively to make it smooth.

This new shape given to the hair by a chemical treatment is long-lasting, lasting a few weeks, and especially withstands the action of washing with water or with shampoos, in contrast with techniques using styling products that result in temporary reshaping, such as hairsetting, which disappears on styling or shampooing the hair.

The reducing compositions generally used for the first step of a permanent-reshaping or straightening operation contain at least one reducing compound in an aqueous medium, and generally ammonia as basifying agent.

However, all these reducing compositions can have a particular drawback. For example, when they are applied to the hair, ammonia can be given off, resulting in an unpleasant odor.

The inventors have surprisingly and unexpectedly found that this release of ammonia can be greatly limited by adding a mesomorphic phase into a reducing composition for permanently reshaping or straightening the hair, comprising at least one reducing compound and ammonia, the mesomorphic phase being present in an amount of at least 10% by weight relative to the total weight of the composition.

Substantial limitation of the release of ammonia is then obtained during the application to the hair of a reducing composition for permanently reshaping or straightening the hair, whether the ammonia is contained in the mesomorphic phase or outside this mesomorphic phase.

It is therefore an aspect of the present disclosure to provide a reducing composition for permanently reshaping or straightening the hair, comprising, in an aqueous medium, at least one reducing compound, ammonia, and greater than or equal to 10% of mesomorphic phase, relative to the total weight of the reducing composition.

It is also an aspect of the present disclosure to provide a process for preparing the reducing composition.

Another aspect of the present disclosure is a process for permanently reshaping or straightening the hair using the reducing composition.

A further aspect of the present disclosure is a multi-compartment device or kit containing the reducing composition.

At least one other aspect, characteristic, or advantage of at least one embodiment of the the invention may emerge upon reading the description and the various examples that follow.

For example, as disclosed herein, the reducing composition for permanently reshaping or straightening the hair, may comprise, in an aqueous medium, at least one reducing compound, ammonia, and at least one mesomorphic phase in an amount greater than or equal to 10% by weight, such as at least 15% by weight, relative to the total weight of the composition.

For instance, the composition may comprise the at least one mesomorphic phase in an amount of less than or equal to 85% by weight, relative to the total weight of the reducing composition.

Significant limitation of the release of ammonia during use of the composition as disclosed herein, is observed whether the ammonia is in the mesomorphic phase or outside this phase.

The term "mesomorphic phase" means a state that is intermediate between a crystalline state and a liquid state. The mesomorphic phase used in the composition as disclosed herein is chosen, for example, from inverse hexagonal phases ($H_2$), lamellar phases ($L_\alpha$ and $L_\beta$), and inverse cubic phases ($I_2$ and $V_2$). For example, a lamellar phase $L_\beta$ may be used in the invention.

The term "inverse hexagonal phase" ($H_2$) means a hexagonal arrangement of parallel cylindrical micelles of amphiphilic molecules (Handbook of Lipid Research 4, The Physical Chemistry Of Lipids From Alkanes To Phospholipids, D. M. Small Editor, 1986, Plenum Press, pp. 51-56).

The term "fluid lamellar phase" (phase $L_\alpha$) means a phase wherein the surfactant molecules and/or more generally the molecules of amphiphilic compounds become organized in the form of bimolecular layers separated by aqueous leaflets. Within the bimolecular layers, the molecules are distributed according to hexagonal or orthorhombic geometry and their fatty chains are in a liquid state, they are oriented perpendicular to the plane of the bimolecular layers, but do not have any specific orientation relative to each other in the plane of these layers (Handbook Of Lipid Research 4, The Physical Chemistry Of Lipids From Alkanes To Phospholipids, D. M. Small Editor, 1986, Plenum Press, pp. 51-56).

The term "gel lamellar phase" (phase $L_\beta$) means a phase in which the surfactant molecules and/or more generally the molecules of amphiphilic compounds become organized in the form of bimolecular layers separated by aqueous leaflets. Within the bimolecular layers, the molecules are distributed according to hexagonal or orthorhombic geometry and their hydrocarbon-based chains are in a crystalline state, they are oriented perpendicular to the plane of the bimolecular layers, but do not have any specific orientation relative to each other in the plane of these layers (Handbook Of Lipid Research 4, The Physical Chemistry Of Lipids From Alkanes To Phospholipids, D. M. Small Editor, 1986, Plenum Press, pp. 51-56).

The term "cubic phase" means a phase organized in a bipolar manner into separate hydrophilic and lipophilic domains, in close contact and forming a cubic symmetry three-dimensional network. Such an organization has been described, for example, in "La Recherche", Vol. 23, pages 306-315, March 1992 and in "Lipid Technology", Vol. 2, No. 2, pages 42-45, April 1990. According to the arrangement of the hydrophilic and lipophilic domains, the cubic phase is said to be of direct or inverse type. The inverse cubic phase corresponds to an oily continuous phase.

The structure of the mesomorphic phase may be checked by polarization microscopy and small-angle X-ray scattering or any other method that it is well known in the art.

As disclosed herein, the mesomorphic phase may comprise, for example, at least one nonionic surfactant with an HLB value of less than or equal to 10, for example ranging from 1 to 5, chosen from monooxyalkylenated, polyoxyalkylenated, monoglycerolated, and polyglycerolated.

The HLB value, or hydrophilic-lipophilic balance, of the at least one nonionic surfactant as disclosed herein is the HLB value according to Griffin defined in the publication J. Soc. Cosm. Chem. 1954 (Volume 5), pages 249-256, or the HLB value determined experimentally and as described in the book by the authors F. Puisieux and M. Seiller, entitled "Galenica 5: Les systèmes dispersés—Tome I—Agents de surface et émulsions—Chapitre IV—Notions de HLB et de HLB critique, pages 153-194—paragraphe 1.1.2. Détermination de HLB par voie expérimentale [Galenica 5: Dispersed systems—Volume I—Surface agents and emulsions—Chapter IV, Notions of HLB and of critical HLB, pages 153-194—paragraph 1.1.2. Determination of HLB experimentally], pages 164-180.

As disclosed herein, the expression "monooxyalkylenated and polyoxyalkylenated nonionic surfactants" means nonionic surfactants comprising in their molecule one or more oxyalkylene groups chosen from the following groups: —$CH_2$—$CH_2$—O—, —$CH_2$—$CH_2$—$CH_2$—O—, and —$CH_2$—$CH(CH_3)$—O—.

As disclosed herein, the expression "monoglycerolated and polyglycerolated nonionic surfactants" means nonionic surfactants comprising in their molecule one or more glycerol groups.

Non-limiting examples of surfactants that may be used as disclosed herein, include those chosen from: polyglycerolated fatty alcohols, monooxyethylenated and polyoxyethylenated fatty alcohols, monoglycerolated and polyglycerolated fatty amides comprising on average from 1 to 5 glycerol groups, monooxyethylenated and polyoxyethylenated alkylphenols, condensates of ethylene oxide and of propylene oxide onto fatty alcohols, polyoxyethylenated vegetal oils, fatty acid esters of polyethylene glycols, and polyoxyethylenated fatty acid esters of sorbitol.

As examples of nonionic surfactants with an HLB greater than 5, non-limiting mention may be made to those sold under the following brand names: Imbentin POA/024 (HLB=5,5) by the company ICI, Synperonic PE L92 (HLB=5,5) by the company ICI, Mergital LM2 (HLB=5.8) by the company Henkel, Atlas G-70140 (HLB=6) by the company ICI, Imbentin. AG/124S/020 (HLB=6) by the company Kolb, Imbentin. L/125/025 HLB=6 by the company Kolb, Simulsol 989 (HLB=6) by the company SEPPIC, Soprophor HR10 (HLB=6) by the company Rhône-Poulenc, Kotilen O/1/050 (HLB=6,2) by the company Kolb, Croduret 10 (HLB=6.3) by the company Croda, Etocas 10 (HLB=6.3) by the company Croda, Imbentin OA/030 (HLB=6.3) by the company Kolb, Soprophor 208 (HLB=6.9) by the company Rhône-Poulenc, Ethylan 172 (HLB=7) by the company Harcros, Akyporox NP 40 (HLB=7.1) by the company Chemy, Polychol 5 (HLB=7.3) by the company Croda, Arlatone 985 (HLB=7.5) by the company ICI, Sandoxylate FOL4 (HLB=7.5) by the company Sandoz, Radiasurf 7453 (HLB=7.8) by the company Oleofina, Prox-onic OA-1/04 (HLB=7.9) by the company Protex, Prox-onic TD-1/03 (HLB=7.9) by the company Protex, Genapol PF 40 (HLB=8) by the company Hoechst, PGE-400-DS (HLB=8) by the company Hefti, PGE-400-DO (HLB=8) by the company Hefti, Sapogenat 6-040 (HLB=8) by the company Hoechst, Intrasol FA28/50/4 (HLB=8.1) by the company Stockhausen, Serdox NOG 200 S (HLB=8.5) by the company Servo, Berol 26 (HLB=8.9) by the company Berol Nobel, Genapol O-050 (HLB=9) by the company Hoechst, Prox-onic LA-1/04 (HLB=9.2) by the company Protex, Eumulgin 05 (HLB=9.5) by the company Henkel, Etocas 20 (HLB=9.6) by the company Croda, Antarox CO 520 (HLB=10) by the company Rhône-Poulenc, Imbentin POA/060 (HLB=10) by the company Kolb, TO-55-EL (HLB=10) by the company Hefti.

As examples of nonionic surfactants with an HLB less than or equal to 5, non-limiting mention may also be made of those sold under the following brand names: Synperonic PE L121 (HLB=0.5) by the company ICI, Prox-Onic EP 4060-1 (HLB=1) by the company Protex, Synperonic PE L101 (HLB=1) by the company ICI, Etocas 29 (HLB=1.7) by the company Croda, Genapol PF 10 (HLB=2) by the company Hoechst, Synperonic PE L81 (HLB=2) by the company ICI, Prox-Onic EP 1090-1 (HLB=3) by the company Protex, Sinnopal DPN2 (HLB=3.3) by the company Henkel, Antarox CA 210 (HLB=3.5) by the company Rhône-Poulenc, Antarox 01 P (HLB=3.5) by the company Rhône-Poulenc, Alkasurf OP11 (HLB=3.6) by the company Rhône-Poulenc, Triton X15 (HLB=3.6) by the company Rohm and Haas, Alkasurf OP1 (HLB=3.6) by the company Rhône-Poulenc, Arlacel 121 (HLB=3.8) by the company ICI, Prox-Onic HR or HRH-05 (HLB=3.8) by the company Protex, Etocas 5 (HLB=3.9) by the company Hoechst, Genapol PF20 (HLB=4) by the company Hoechst, Imbentin N/7 A (HLB=4) by the company Kolb, Synperonic PE L122 (HLB=4) by the company ICI, Ethylan NP1 (HLB=4.5) by the company Harcros, Imbentin N/020 (HLB=4.5) by the company Kolb, Kotilen 0/3/020 (HLB=4.5) by the company Kolb, Synperonic PE L31 (HLB=4.5) by the company ICI, TO-55-A (HLB=4.5) by the company Hefti, Alkasurf NP-1 (HLB=4.6) by the company Rhône-Poulenc, Antarox CO 210 (HLB=4.6) by the company Rhône-Poulenc, Prox-Onic NP-1 (HLB=4.6) by the company Protex, Rhodiasurf NP2 (HLB=4.6) by the company Rhône-Poulenc, Soprophor BC2 (HLB=4.6) by the company Rhône-Poulenc, Triton N17 (HLB=4.6) by the company Rohm and Haas, Akyporox NP15 (HLB=4.7) by the company Chem-y, Texofor M2 (HLB=4.8) by the company Rhône-Poulenc, Alkasurf SA2 (HLB=4.9) by the company Rhône-Poulenc, Arlacel 989 (HLB=4.9) by the company ICI, Brij 72 (HLB=4.9) by the company ICI, Brij 92 (HLB=4.9) by the company ICI, Brij 93 (HLB=4.9) by the company ICI, Prox-Onic SA-1 or 2/02 (HLB=4.9) by the company Protex, Simulsol 72 (HLB=4.9) by the company SEPPIC, Simulsol 92 (HLB=4.9) by the company SEPPIC, Volpo S-2 (HLB=4.9) by the company Croda, Arlacel 581 (HLB=5.0) by the company ICI, Arlacel 582 (HLB=5.0) by the company ICI, Genapol 0-020 (HLB=5.0) by the company Hoechst, Imbentin POA/020 (HLB=5.0) by the company Kolb, and Mergital Q2 (HLB=5.0) by the company Henkel.

For example, a nonionic surfactant that may be suitable for use as disclosed herein is hexadecyl alcohol containing 2 mol of glycerol.

The at least one nonionic surfactant may be present in an amount ranging from 5% to 30% by weight, such as from 5.5% to 30% by weight, and further such as from 10% to 20% by weight, relative to the total weight of the reducing composition.

The mesomorphic phase may also comprise at least one fatty alcohol comprising from 8 to 30 carbon atoms, such as, from 12 to 22 carbon atoms. For example, the at least one fatty alcohol may be hexadecanol.

The fatty alcohol may be present in an amount ranging from 3% to 20% by weight, for example, from 5% to 15% by weight, relative to the total weight of the reducing composition.

As disclosed herein, the ammonia may be present in the reducing composition in an amount ranging from 0.01% to 4% by weight, such as from 0.05% to 2% by weight, relative to the total weight of the composition.

Non-limiting examples of keratin-reducing compounds that may be used include alkali metal, alkaline-earth metal, ammonium sulphites, ammonium bisulphites, and thiols.

Among the thiols that may be used, non-limiting mention can be made of cystein and derivatives thereof (such as N-acetylcysteine), cysteamine and its various derivatives (such as its $C_1$-$C_4$ acyl derivatives such as N-acetylcysteamine and N-propionylcysteamine), thiolactic acid and its esters (such as glyceryl monothiolactate), thioglycolic acid and its esters, such as glyceryl monothioglycolate and glycol monothioglycolate, and thioglycerol. Mention may also be made of the following reducing compounds: sugar N-mercaptoalkylamides such as N-(2-mercaptoethyl)gluconamide, β-mercaptopropionic acid and its derivatives, thiomalic acid, pantetheine, the N-(mercaptoalkyl)-ω-hydroxyalkylamides described in patent application EP-A-354,835 and the N-mono- or N,N-dialkylmercapto-4-butyramides described in patent application EP-A-368,763, the aminomercaptoalkylamides described in patent application EP-A-432,000 and the alkylaminomercaptoalkylamides described in patent application EP-A-514,282, the mixture of 2-hydroxypropyl thioglycolate (⅔) and of 2-hydroxy-1-methylethyl thioglycolate (67/33) described in patent application FR-A-2,679, 448.

Among the reducing compounds that can be used in the composition disclosed herein, non-limiting mention may be made of thioglycolic acid and cysteine.

Among the reducing compositions for permanently reshaping or straightening the hair that can be used in the composition disclosed herein, the reducing compounds as mentioned above are generally present in a concentration ranging from 0.1% to 30% by weight, for example from 1% to 20% by weight, relative to the total weight of the reducing composition.

As disclosed herein, the reducing compositions may also comprise common conventional additives chosen from surfactants other than those mentioned above, of nonionic, anionic, cationic and amphoteric type. Among the surfactants non-limiting mention may be made of alkyl sulphates, alkyl benzenesulphates, alkyl ether sulphates, alkyl sulphonates, quaternary ammonium salts, alkylbetaines, fatty acid alkanolamides, oxyethylenated fatty acid esters, and also other nonionic surfactants of the hydroxypropyl ether type.

When the reducing composition contains, in addition to the nonionic surfactants with an HLB value of less than or equal to 10, at least one surfactant, this surfactant is generally present in a maximum concentration of 30% by weight, such as ranging from 0.5% to 10% by weight relative to the total weight of the reducing composition.

With the aim, for example, of improving the cosmetic properties of the hair or of attenuating or preventing its degradation, the reducing composition may also contain a treating agent chosen from cationic, anionic, nonionic, and amphoteric treating agents.

Among the treating agents non-limiting mention may be made to those described in FR 2,598,613 and FR 2,470,596. Treating agents that may also be used include volatile and non-volatile, linear and cyclic silicones and mixtures thereof, polydimethylsiloxanes, quaternized polyorganosiloxanes such as those described in FR 2,535,730, polyorganosiloxanes containing aminoalkyl groups modified with alkoxycarbonylalkyl groups, such as those described in U.S. Pat. No. 4,749,732, which is herein incorporated by reference, polyorganosiloxanes such as the polydimethylsiloxane-polyoxyalkyl copolymer of the Dimethicone Copolyol type, a polydimethylsiloxane containing stearoxy-(stearoxydimethicone) end groups, polydimethylsiloxane-dialkylammonium acetate copolymers and polydimethylsiloxane-polyalkylbetaine copolymers described in British patent application number 2,197,352, polysiloxanes organomodified with at least one group chosen from mercapto and mercaptoalkyl groups, such as those described in FR 1,530,369 and in EP 295,780, and also silanes such as stearoxytrimethylsilane.

As disclosed herein, the reducing composition may also contain other treating ingredients including cationic polymers, such as those used in the compositions of FR 2,472,382 and FR 2,495,931, or alternatively cationic polymers of the ionene type, such as those used in the compositions of Luxembourg patent 83703, basic amino acids (such as lysine or arginine), acidic amino acids (such as glutamic acid and aspartic acid), peptides and derivatives thereof, protein hydrolysates, waxes, swelling agents, penetrating agents, agents for improving the efficacy of the reducing agent, such as the $SiO_2$/PDMS (polydimethylsiloxane) mixture, dimethylisosorbitol, urea and its derivatives, pyrrolidone, N-alkylpyrrolidones, thiamorpholinone, alkylene glycol or dialkylene glycol alkyl ethers, for instance propylene glycol monomethyl ether, dipropylene glycol monomethyl ether, ethylene glycol monoethyl ether and diethylene glycol monoethyl ether, $C_3$-$C_6$ alkanediols, for instance 1,2-propanediol and 1,2-butanediol, 2-imidazolidinone, and also other compounds such as pantothenic acid, agents for preventing hair loss, antidandruff agents, thickeners, suspension agents, sequestering agents, opacifiers, colorants, sunscreens, and also fragrances and preserving agents.

The reducing composition may be in the form of an optionally thickened lotion, a cream or a gel, or in any other suitable form.

As disclosed herein, the aqueous medium may be chosen from water and aqueous-alcoholic solutions of a $C_{1-4}$ lower alcohol, such as ethanol, isopropanol, and butanol.

In an aspect of the present disclosure, the aqueous medium contains no organic solvent.

When the compositions are intended for a straightening or uncurling operation on the hair, the reducing composition may be in the form of a thickened cream so as to keep the hair as stiff as possible. These creams may be prepared in the form of "heavy" emulsions, the oily phase of which may comprise various products such as liquid paraffin, liquid petroleum jelly, sweet almond oil, avocado oil, olive oil, fatty acid esters, for instance glyceryl monostearate, ethyl palmitate, isopropyl palmitate, and alkyl myristates such as propyl myristate, butyl myristate, and cetyl myristate. Fatty alcohols, for instance cetyl alcohol, and waxes, for instance beeswax, may also be added.

Liquids or gels containing thickeners, such as carboxyvinyl polymers and copolymers, which "stick" the hairs together and keep them in a smooth position during the leave-in time, may also be used.

Finally, the reducing compositions may also comprise at least one disulphide known for its use in a self-neutralizing permanent-waving reducing composition.

Among such known disulphides, non-limiting mention may be made of dithioglycolic acid, dithioglycerol, cystamine, N,N'-diacetylcystamine, cysteine, pante-theine, and the N-(mercaptoalkyl)-ω-hydroxyalkylamide disulphides described in European patent application EP 354,835, the N-mono- and N,N-dialkylmercapto-4-butyramide disulphides described in patent application EP 368,763, the aminomercaptoalkylamide disulphides described in patent application EP 432,000, and the alkylaminomercaptoalkylamide disulphides described in patent application EP 514 282. As described in U.S. Pat. No. 3,768,490, the contents of which are herein incorporated by reference, these disulphides are generally present in a molar ratio ranging from 0.5:1 to 2.5:1, such as from 1:1 to 2:1, relative to the reducing agent.

The pH of the reducing compositions may optionally be adjusted by adding acidifying agents, for instance hydrochloric acid, acetic acid, lactic acid, and boric acid, and basifying agents other than ammonia.

The pH, for example, generally ranges from 6 to 10, for further example, from 7 to 9.5.

Another aspect of the present disclosure is a process for preparing the reducing composition described herein. The process comprises:
(a) mixing at least one nonionic surfactant with an HLB value of less than or equal to 10, for example, ranging from 1 to 5, with water and optionally with one or more fatty alcohols, to prepare a mesomorphic phase, and
(b) adding at least one reducing compound as described herein.

Ammonia is added in (a) and/or in (b). In other words, ammonia may be added either at the time of preparation of the mesomorphic phase, or it may already be present in the medium of the reducing composition before addition of the mesomorphic phase, or it may be added to the reducing composition after incorporation of the mesomorphic phase.

Another aspect of the present disclosure comprises incorporating a mesomorphic phase comprising ammonia into a medium that itself comprises ammonia.

Another aspect of the present disclosure comprises a process for permanently reshaping or straightening the hair, comprising:
(a) applying a reducing composition as disclosed herein, during or after the placing the hair under tension either mechanically or by manually shaping;
(b) applying, after a leave-in time that is sufficient to allow the reduction of the disulphide bonds of the hair, and after optional rinsing, an oxidizing composition comprising at least one oxidizing agent; and
(c) performing a final rinse with water.

Placing the hair under tension may be performed via any suitable and known mechanical procedures, such as rollers and curlers.

As disclosed herein, the oxidizing agent may be chosen from, for instance, hydrogen peroxide, aqueous hydrogen peroxide solution, urea peroxide; alkali metal bromates; persalts such as perborates and persulphates; and enzymes, such as peroxidases and two-electron oxidoreductases. For example, the at least one oxidizing agent may be chosen from hydrogen peroxide and the bromates.

The concentration of aqueous hydrogen peroxide solution may range from 1 to 10 volumes, for example about 8 volumes.

The concentration of bromates generally ranges from 1% to 12% by weight, and the concentration of persalts generally ranges from 0.1% to 15% by weight, relative to the total weight of the oxidizing composition.

The pH of the oxidizing composition generally ranges, for example, from 2 to 7, for further example from 3 to 6.

The invention also relates to a multi-compartment kit for permanently reshaping or straightening keratin fibers, such as hair, comprising at least two compartments, one of which contains a reducing composition as disclosed herein, and one of which contains an oxidizing composition.

The examples that follow are given as illustrations of the invention.

EXAMPLES

Example 1

Preparation of a Lamellar Mesomorphic Phase $L_\beta$

Water and ammonia were added to a mixture of hexadecyl alcohol containing 2 mol of glycerol ($C_{16}G_2$) and hexadecanol ($C_{16}OH$), the proportions being indicated in Table 1 below. The structure was subjected to three 2-hour heating cycles, varying the temperature from room temperature to a temperature of about 70° C., with stirring to produce a lamellar mesomorphic phase $L_\beta$ that can be used in accordance with the invention.

An aqueous composition was also prepared to serve as control, and a dispersion of the lamellar phase $L_\beta$ in water (or dispersion $L_\beta$) was prepared that can be used according to the invention.

TABLE 1

| | Weight % | | | |
| --- | --- | --- | --- | --- |
| | $C_{16}G_2$ | $C_{16}OH$ | $NH_3$ | Water |
| Aqueous composition | — | — | 1 | 99 |
| Lamellar phase $L_\beta$ | 52.5 | 32.5 | 1 | 14 |
| Dispersion $L_\beta$ | 10.5 | 6.5 | 1 | 82 |

The structure of the lamellar phase was checked by polarization microscopy and small-angle X-ray diffusion.

The release of ammonia was then measured with colorimetric tubes, on samples of 10 ml of each of the compositions, contained in 30 ml open flasks the values being indicated in Table 2 below. The resulting uncertainty is at most about 10%. The measurements for each sample lasted 20 to 30 seconds.

TABLE 2

| | Release of $NH_3$ (ppm) after | | | |
| --- | --- | --- | --- | --- |
| | 1 min. | 5 min. | 10 min. | 20 min. |
| Aqueous composition | >1400 | 1367 | 1300 | 1133 |
| Lamellar phase $L_\beta$ | 433 | 283 | 183 | 133 |
| Dispersion $L_\beta$ | 533 | 333 | 367 | 350 |

The sample of lamellar phase diffused from 3 to 8 times less than the control sample. The dispersion of the lamellar phase in excess water presented a release that was 3 to 4 times less than that of the control sample. This result was found whether the ammonia was present in the mesomorphic phase before dispersion or in the dispersion water.

Example 2

Preparation of a Reducing Composition

A reducing composition according to the present disclosure was prepared by mixing, at room temperature (about 20-25° C.), 100 g of the lamellar phase as prepared in example 1, and 15 g of a waving medium, the components thereof being indicated below.

The components of the reducing composition, including the components of the lamellar phase, are indicated in Table 3 below, with weight proportions thereof relative to the total weight of the reducing composition.

TABLE 3

| Components of th reducing composition: | Weight % |
|---|---|
| Ammonium bicarbonate | 5.3 |
| Pentasodium salt of diethylenetriamine-pentacetic acid in 40% aqueous solution | 0.17 |
| (20 EO) oxyethylenated oleocetyl alcohol | 0.67 |
| Perfume | 0.33 |
| Mixture cocoylamidopropylbetaine/glyceryl monolaurate in 30% aqueous solution | 1.1 |
| Polydimethylsiloxane with aminoethyl, aminopropyl and alpha-omega-silanol groups, cationic emulsion | 2.2 |
| Ammonium thioglycolate in 71% aqueous solution | 12.8 |
| Tetramethyl-hexamethylenediamine/ 1,3-dichloro-propylene polycondensate in 60 % aqueous solution | 1.3 |
| Ammonia (20%) | 2.0 |
| Hexadecyl alcohol containing 2 moles of glycerol | 8.8 |
| Hexadecanol | 5.4 |
| Deionized water | qs 100 |

A significant reduction of the ammonia release was observed over time.

What is claimed is:

1. A reducing composition for permanently reshaping or straightening the hair, comprising, in an aqueous medium, at least one keratin-reducing compound, ammonia, and at least one mesomorphic phase present in an amount ranging from 10% to 85% by weight, relative to the total weight of the reducing composition,
wherein the at least one mesomorphic phase comprises wherein the nonionic surfactant is hexadecyl alcohol comprising 2 mol of glycerol nonionic surfactant with an HLB value of less than or equal to 10 in an amount ranging from 10% to 20% by weight, relative to the total weight of the reducing composition.

2. The reducing composition according to claim 1, wherein the at least one mesomorphic phase is a lamellar phase $L_\beta$.

3. The reducing composition according to claim 1, wherein the at least one mesomorphic phase further comprises at least one fatty alcohol comprising from 8 to 30 carbon atoms.

4. The reducing composition according to claim 3, wherein the at least one fatty alcohol is hexadecanol.

5. The reducing composition according to claim 3, wherein the at least one fatty alcohol is present in an amount ranging from 3% to 20% by weight, relative to the total weight of the reducing composition.

6. The reducing composition according to claim 5, wherein the at least one fatty alcohol is present in an amount ranging from 5% to 15% by weight, relative to the total weight of the reducing composition.

7. The reducing composition according to claim 1, wherein the ammonia is present in an amount ranging from 0.01% to 4% by weight relative to the total weight of the reducing composition.

8. The reducing composition according to claim 7, wherein the ammonia is present in an amount of from 0.05% to 2% by weight, relative to the total weight of the composition.

9. The reducing composition according to claim 1, wherein the keratin-reducing compound is chosen from alkali metal, alkaline-earth metal, ammonium sulphites, ammonium bisulphites, and thiols.

10. The reducing composition according to claim 9, wherein the keratin-reducing compound is chosen from thioglycolic acid and cysteine.

11. The reducing composition according to claim 1, wherein the keratin-reducing compound is present in an amount ranging from 1% to 30% by weight, relative to the total weight of the reducing composition.

12. The reducing composition according to claim 11, wherein the keratin-reducing compound is present in an amount ranging from 5% to 20% by weight, relative to the total weight of the reducing composition.

13. The reducing composition according to claim 1, wherein the aqueous medium is chosen from water and aqueous-alcoholic solutions of at least one $C_{1-4}$ lower alcohol.

14. The reducing composition according to claim 13, wherein said at least one $C_{1-4}$ lower alcohol is chosen from ethanol, isopropanol, and butanol.

15. A process for preparing a reducing composition, comprising, in an aqueous medium, at least one keratin-reducing compound, ammonia, and at least one mesomorphic phase present in an amount ranging from 10% to 85% by weight, relative to the weight of the reducing composition, said process comprising:
(a) mixing nonionic surfactant with an HLB value of less than or equal to 10, with water and optionally with one or more fatty alcohols, to prepare said at least one mesomorphic phase wherein the nonionic surfactant is hexadecyl alcohol comprising 2 mol of glycerol, and
(b) adding at least one reducing compound,
wherein said ammonia is added in (a) and/or (b).

16. A process for permanently reshaping or straightening hair, said process comprising:
(a) applying to the hair, a composition according to claim 1, further wherein said composition is applied to the hair during or after placing the hair under tension,
(b) leaving said composition in the hair for a time that is sufficient to allow reduction of the disulphide bonds of the hair,
(c) applying an oxidizing composition containing at least one oxidizing agent to the hair, and
(d) rinsing the hair with water.

17. The process according to claim 16, wherein the hair is placed under tension mechanically or by manually shaping.

18. The process according to claim 16, wherein the hair is rinsed with water prior to applying said oxidizing composition.

19. The process according to claim 16, wherein the oxidizing agent is chosen from alkali metal bromates and hydrogen peroxide.

20. A multi-compartment kit for permanently reshaping or straightening the hair, comprising at least two compartments, wherein at least one compartment contains a reducing composition according to claim 1, and another compartment contains an oxidizing composition.

* * * * *

UNITED STATES PATENT AND TRADEMARK OFFICE
CERTIFICATE OF CORRECTION

| | | |
|---|---|---|
| PATENT NO. | : 7,867,478 B2 | Page 1 of 1 |
| APPLICATION NO. | : 10/745366 | |
| DATED | : January 11, 2011 | |
| INVENTOR(S) | : Lu Nicholas-Morgantini et al. | |

It is certified that error appears in the above-identified patent and that said Letters Patent is hereby corrected as shown below:

Claim 1, col. 9, line 46, "wherein the at least one mesomorphic phase comprises wherein the nonionic surfactant is hexadecyl alcohol comprising 2 mol of glycerol nonionic surfactant with an HLB value of less than or equal to 10 in an amount ranging from 10% to 20% by weight, relative to the total weight of the reducing composition."

should read

-- wherein the at least one mesomorphic phase comprises nonionic surfactant with an HLB value of less than or equal to 10 in an amount ranging from 10% to 20% by weight, relative to the total weight of the reducing composition wherein the nonionic surfactant is hexadecyl alcohol comprising 2 mol of glycerol. --

Signed and Sealed this
Twenty-sixth Day of June, 2012

David J. Kappos
*Director of the United States Patent and Trademark Office*